(12) United States Patent
N'Guyen et al.

US006316012B1

(10) Patent No.: US 6,316,012 B1
(45) Date of Patent: Nov. 13, 2001

(54) COSMETIC OR PHARMACEUTICAL COMPOSITION COMPRISING, IN COMBINATION, A PEROXIDASE AND AN ANTI-SINGLET OXYGEN AGENT

(75) Inventors: Quang lan N'Guyen, Antony; Christian Colin, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/413,496

(22) Filed: Oct. 6, 1999

Related U.S. Application Data

(63) Continuation of application No. 08/923,398, filed on Sep. 4, 1997, now abandoned, which is a continuation of application No. 08/476,060, filed on Jun. 7, 1995, now abandoned, which is a continuation of application No. 08/109,266, filed on Aug. 20, 1993, now abandoned.

(30) Foreign Application Priority Data

Sep. 1, 1992  (FR) .................................................. 92 10439

(51) Int. Cl.[7] .................................................. A61K 38/43
(52) U.S. Cl. ........................ 424/401; 424/78.02; 424/59; 424/94.1; 514/937; 514/844
(58) Field of Search ........................ 424/401, 59, 78.02, 424/94.1; 514/844, 937

(56) References Cited

U.S. PATENT DOCUMENTS

| | | |
|---|---|---|
| 4,129,644 | 12/1978 | Kalopissis . |
| 4,473,550 | 9/1984 | Rosenbaum et al. . |
| 4,609,544 | 9/1986 | Herlihy . |
| 4,956,184 | 9/1990 | Kross . |
| 5,023,235 | 6/1991 | N'Guyen . |
| 5,244,497 | 9/1993 | Junino . |
| 5,362,494 | 11/1994 | Zysman . |
| 5,474,777 | 12/1995 | Marion et al. . |
| 5,686,082 | * 11/1997 | N'Guyen .............................. 424/401 |

FOREIGN PATENT DOCUMENTS

| | | |
|---|---|---|
| 0307626 | 3/1989 | (EP) . |
| 0397227 | 11/1990 | (EP) . |
| 2112550 | 6/1972 | (FR) . |
| 2315991 | 1/1977 | (FR) . |
| 2378796 | 8/1978 | (FR) . |
| 2400358 | 3/1979 | (FR) . |
| 2400359 | 3/1979 | (FR) . |
| 2416008 | 8/1979 | (FR) . |
| 02620024 | 3/1989 | (FR) . |
| 0111411 | 8/1980 | (JP) . |
| 03-236320 | 10/1991 | (JP) . |
| 05-124980 | 10/1991 | (JP) . |
| 87/07838 | 12/1987 | (WO) . |
| 88/02600 | 4/1988 | (WO) . |
| 91/06639 | 5/1991 | (WO) . |
| 92/01466 | 2/1992 | (WO) . |

OTHER PUBLICATIONS

Igarashi, Osamu, "Vitamin E Focusing on Antioxidative Activity, Biological Activity of Vitamin E Analogues, Transportation in Blood, and Distribution in Tissues and Organs," *Institute of Environmental Science for Human Life*, 1991.
Database WPIL Week 8943, Derwent Publications Ltd., London, GB; AN 89–310020 & DD–A–268 157.
D.L. Bissett et al., "Protective Effect of Topically Applied Conjugated Hexadienes Against Ultraviolet Radiation–Induced Chronic Skin Damage in the Hairless Mouse," *Photoderm. Photoimmunol. Photomed.*, 1990: 7: pp. 63–67.
D.L. Bissett et al., "Photoprotective Effect of Superoxide–Scavenging Antioxidants Against Ultraviolet Radiation–Induced Chronic Skin Dasmage in the Hairless Mouse," *Photoderm. Photoimmunol. Photomed.*, 1990: 7: pp. 56–62.
*American Health*, Jul./Aug. 1994, p. 72.

\* cited by examiner

*Primary Examiner*—Raj Bawa
(74) *Attorney, Agent, or Firm*—Oliff & Berridge, PLC

(57) ABSTRACT

A method of preventing damage caused to healthy skin, hair or mucous membranes by free radicals, includes applying to the healthy skin, hair or mucous membrane a composition containing at least one product having a peroxidase activity capable of reducing organic peroxides and at least one antioxidant capable of neutralizing singlet oxygen, the composition being free of peroxide. The product having a peroxidase activity is present in an amount of from 0.005 to 5.0% by weight, and the antioxidant is present in an amount of from 0.005 to 3.0% by weight, with a weight ratio of the product having a peroxidase activity to the antioxidant of from 0.001 to 0.3. The product having a peroxidase activity capable of reducing organic peroxides is lactoperoxidase, and the antioxidant is selected from quinolines, polyphenols, and carotenoids.

11 Claims, No Drawings

COSMETIC OR PHARMACEUTICAL COMPOSITION COMPRISING, IN COMBINATION, A PEROXIDASE AND AN ANTI-SINGLET OXYGEN AGENT

This is a Continuation of application Ser. No. 08/923,398 filed Sep. 4, 1997 now abandoned, which in turn is a Continuation of application Ser. No. 08/476,060 filed Jun. 7, 1995 now abandoned, which in turn is a Continuation of application Ser. No. 08/109,266 filed Aug. 20, 1993 now abandoned. The entire disclosures of the prior applications are hereby incorporated by reference herein in their entirety.

The subject of the invention is a synergistically acting cosmetic or pharmaceutical composition containing, in combination, a peroxidase and an antioxidant Specialists currently consider that one of the causes of cellular aging is the reduction in the defence capacities against free radicals and against the oxidation phenomena (especially the formation of peroxides) which they initiate.

It is known moreover that the toxicity of atmospheric pollutants, especially gaseous pollutants such as sulphur dioxide, ozone and nitrogen oxides, is linked especially to their free radical-initiating activity, source of oxidation phenomena which cause, in living beings, cellular damage.

Living cells, which are in direct and permanent contact with the external medium (especially the skin, the scalp and certain mucous membranes), are particularly sensitive to these effects of gaseous pollutants, which result especially in an accelerated aging of the skin, with a complexion lacking brightness and a premature formation of wrinkles or small wrinkles, and also in a decrease in the vitality and a dull appearance of the hair.

It is also known that the irritation phenomena caused by exposure to ultraviolet rays also lead to the phenomenon of accelerated cellular aging, and are currently considered as a factor for inducing skin tumours. The irritation caused by UV radiation gives rise, in this case as well, to the formation of radical species which lead especially to the oxidation of skin lipids, and it is thought that lipid peroxides are one of the factors which trigger photocarcinogenesis. It is known in particular that the induction of ornithine decarboxylase (abbreviated ODC) constitutes an early marker for skin tumour, and that organic peroxides are capable of inducing the formation of ODC in the epidermis; see R. L. Binder et al., Carcinogenesia, Vol. 10, No.12, 2351–2357 (1989).

Living cells possess various natural means of defence against lipid peroxides, in particular epidermal glutathione peroxidase, but the effectiveness of the detoxifying activity of the latter is substantially decreased under the influence of an exposure to ultraviolet radiation.

It in therefore important to develop active systems which make it possible to combat the harmful effects of peroxides, especially the organic peroxides formed under the action of atmospheric pollutants and ultraviolet radiation.

It is known that some antioxidant are capable of conferring a protection against the skin damage caused by radiations or peroxides, including when theme antioxidants are applied topically; see for example Bissett at al., Photoderm. Photoimmunol. Photomed. 7,56–62 and 63–67 (1990).

By studying certain antioxidant systems and by using the induction of ODC as marker, the Applicant has discovered that, surprisingly, certain combinations had the property of inhibiting the formation of ODC while the constituents of the combination, when used alone, had no effect or even caused an increase in the induction of ODC.

It has been discovered more precisely that the peroxidases capable of reducing organic peroxides cause an increase in the induction of ODC by ultraviolet radiation, and that certain antioxidant are without significant effect on the induction of ODC. Such in the came especially for the antioxidant. capable of neutralizing singlet oxygen, which are therefore anti-singlet oxygen agents. It has however been discovered that the combination of peroxidases capable of reducing organic peroxides with antioxidants capable of neutralizing singlet oxygen, makes it possible to substantially neutralize the induction of ODC. Such a combination therefore has synergistic properties.

These useful properties can be exploited by incorporating such synergistic combinations into cosmetic or pharmaceutical compositions in a form which allows application to the skin, superficial body growths and mucous membranes.

The subject of the invention is therefore a cosmetic or pharmaceutical composition characterized by the fact that it comprises, in combination, at least one product having a peroxidase activity capable of reducing organic peroxides and at least one antioxidant capable of neutralizing singlet oxygen.

The composition of the invention in an antioxidant composition which therefore does not contain peroxide. In particular, it does not contain hydrogen peroxide.

There may be used as product having a peroxidase activity any substance capable of reducing organic peroxides in the presence of an electron donor.

These peroxidases may be especially peroxidases of natural (plant or animal) origin, or alternatively peroxidases modified chemically or by grafting, by adsorption onto supports or by encapsulation (see for example applications PCT WO 87/07838 and EP-A-0,397,227).

There may be used especially lactoperoxidases, fungal microperoxidases, myoloperoxidase and the like.

It in known that lactoperoxidase (abbreviated LPO) is an enzyme which occurs especially in numerous mammalian tissues and secretions, which uses one of the numerous cellular electron donors to reduce organic peroxides of the ROOH typo (R being an organic group). Lactoperoxidase is a commercial product, sold especially by the companies Sigma and Sederma.

There may be also used recombinant peroxidases, for example recombinant LPO (Patent Application Wo 91-06639).

The antioxidant capable of neutralizing singlet oxygen is chosen especially from quinoline and its derivatives, polyphonols, carotenoid derivatives and nucleosides and their derivatives.

Among the quinoline derivatives which can be used, there may be mentioned in particular 6-athoxy-1,2-dihydro-2,2,4-trimethylquinoline or ethoxyquine, in the form of a monomer, dimer or oligomer or mixtures of these various forms, and ethoxyquine derivatives.

There may be used in particular the ethoxyquine derivatives of formula (I)

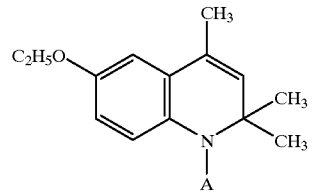

(I)

in which A represents a group —CO—B,

B representing especially a group $(CHOR')_n R$ in which R' represents a hydrogen atom, an acyl, alkyl or aralkyl group, R is a hydroxymethyl, carboxyl, carboxyalkyl, carboxyaryl, carboxyarylalkyl, carboxamide or —COR''' group, R''' representing ethoxyquine residue (formula (I) less the substituent A) or R''' representing —CR$_2$OR'', R'' being an acyl, aralkyl or alkyl radical and n being an integer from 2 to 6;

or B represents a group —(CHR'''')$_m$N$^+$R$_1$R$_2$R$_3$X$^-$ in which R'''' represents a hydrogen atom, an optionally substituted heterocyclic, aralkyl, aryl or alkyl radical, or R'''' represents —(CH$_2$)$_q$COOH where q is a number which may vary from 1 to 3, R$_1$, R$_2$ and R$_3$ independently representing a hydrogen atom, an aryl radical, a heterocyclic aryl radical, a substituted or unsubstituted cycloalkyl or alkyl radical, X$^-$ being an anion and m being an integer from 1 to 6;

or B represents a group —(CHR'''')$_m$ NR$_1$R$_2$, where R'''', R$_1$, R$_2$ and m have the meanings stated above;

or B represents a group NR'$_1$R'$_2$ in which R'$_1$ and R'$_2$ independently represent a substituted or unsubstituted aryl, heterocyclic aryl, cycloalkyl or alkyl group or alternatively R'$_1$ and R'$_2$ represent —H or form a heterocyclic group with the nitrogen atom to which they are attached;

or B represents a group —OR$_4$ in which R$_4$ represents an aryl, alkyl, polyhydroxyalkyl or cycloalkyl group or a group of formula

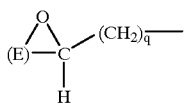

where E represents a group:

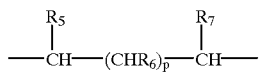

in which R$_5$, R$_6$ and R$_7$ independently represent a hydrogen atom or a radical —CH$_2$OH, —CH$_2$O acyl, —OH, —O acyl, —NH acyl, —NH$_2$, N$^+$H$_3$X$^-$, X$^-$ being defined an above, or alternatively R$_5$, R$_6$ and R$_7$ represent a group —COOR$_8$, R$_8$ representing a hydrogen atom, a substituted or unsubstituted aralkyl, aryl, cycloalkyl or alkyl group, p is a number equal to 1 or 2 and q is equal to 0 or 1;

or B represents a halogen atom, or alternatively A represents a group:

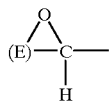

in which E is defined as above.

Such ethoxyquine derivatives are described especially in Patent Application FR-2,378,796.

Among the agents capable of neutralizing singlet oxygen, there may be also mentioned polyphenols, that is to say the compounds comprising at least one diphenolic aromatic ring, it being possible for the phenol groups to be optionally etherified or esterified. Among the polyphenols which can be used, there may be mentioned especially the flavonoids corresponding to the general formula (II):

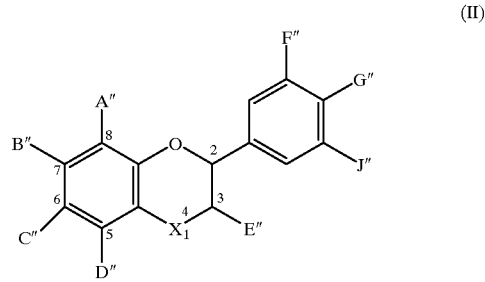

or (III):

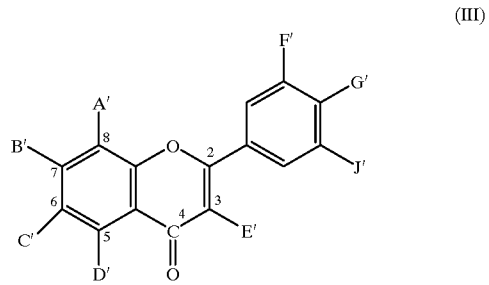

in which A'', B'', C'' and D'', independently of each other, represent H or OH; E'' represents H, OR or OX', where X' represents:

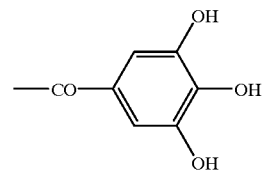

F'', G'', J'' represent, independently of each other, H or OH; and X$_1$ represents —CH$_2$—, —CO— or —CHOH—, it being understood that at least two of the groups A'', B'', C'' and D'' or at least two of the radicals F'', G'' and J'' designate a hydroxyl group, A', C' and D', independently of each other, represent H, OH or OCH$_3$;

E' represents H, or OR', where R' represents the residue of a sugar of formula R'OH;

B', F', G' and J', independently of each other, represent H, OH, OCH$_3$ or —OCH$_2$—CH$_2$—OH, it being understood that at least two of the groups A', B', C' and D' do not designate —H or that at least one of the groups F', G' and J' does not designate —H.

Among the sugars R'OH, rutinose may be mentioned.

The compounds of formula (II) and (III) are known. They may be obtained especially according to the procedures described in "The Flavonoids" Harborne J. B., Mabry T. J., Helga Mabry, 1975, pages 1 to 45.

Among the flavonoids which can be used according to the invention, there may be mentioned especially taxifoline, catechin, epicatechin, eriodictyol, naringenin, rutin, troxerutin, chrysin, tangeretine, luteolin, opigallocatechin, epigallocatechin gallate, quercetin, fisetin, kaempferol, galangin, gallocatechin and epicatechin gallate.

Such compounds occur especially in the green tea extracts sold under the name Sunphenon by the company Nikko.

Among the polyphonols which can be used, there may be also mentioned polyphenols such as carnosic acid and carnosol which may be extracted for example from rosemary either by extraction followed by a distillation (Chang et al. JOSC, Vol. 61, No.6, June 1984), or by an extraction with a polar solvent such as ethanol preceded by an extraction by means of. a non-polar solvent such as hexane in order to remove odorous substances, as described in Patent Application EP-307 626.

The polyphenols which may be used may also be chosen from the (2,5-dihydroxyphenyl)alkylcarboxylic acids of formula (IV) and their derivatives (especially esters and amides):

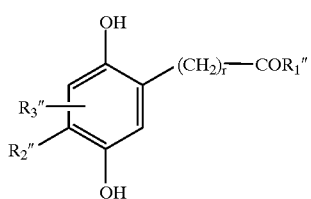

(IV)

in which:

- $R''_1$ represents —O—Alc, OH or —N(r')(r''), Alc being a linear or branched $C_1$–$C_{20}$ alkyl optionally substituted by one or more hydroxyl or alkoxy groups, or Alc being a $C_2$–$C_{20}$ alkenyl,
- r' and r'' independently represent H, $C_1$–$C_{20}$ alkyl, $C_2$–$C_6$ hydroxyalkyl or $C_3$–$C_6$ polyhydroxyalkyl, or alternatively r' and r'' together form, with the nitrogen atom to which they are attached, a heterocycle,
- r in a number, including zero, such that the chain —$(CH_2)_r$—$COR_1$ comprises at most 21 carbon atoms,
- $R''_2$ and $R''_3$ independently represent H or a $C_1$–$C_4$ alkyl, it being possible for $R''_2$ to represent, in addition, a $C_1$–$C_4$ alkoxy.

The compounds of formula (IV) are known or can be prepared according to known methods, for example analogous to those described in Patents FR-2,400,358 and FR-2,400,359.

Among the polyphenols which can be used according to the invention, there may be also mentioned the esters or amides of caffeic acid. Among the asters of caffeic acid, there may be mentioned especially the compounds of formula (V):

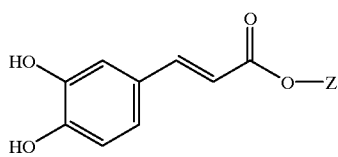

(V)

in which Z represents a $C_1$–$C_8$ alkyl, for example methyl, or the residue of a phytol.

Among the amides of caffeic acid, there may be mentioned especially the compounds of formula (VI):

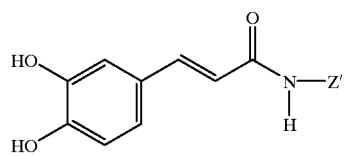

(VI)

in which Z' represents a $C_1$–$C_8$, in particular $C_6$–$C_8$, alkyl.

The compounds of formula (V) or (VI) are known or can be prepared according to known methods.

Among the antioxidant. capable of neutralizing singlet oxygen, there may be also mentioned carotenoid derivatives, and in particular the following compounds:

All-trans-betacarotono,
alpha-carotene,
gamma-carotene,
delta-carotene,
docapreno-beta-carotene,
dodecaprono-beta-carotene
lycopen,
zaxanthin,
astaxanthin,
violaxanthin,
lutein,
bixin,
canthaxnthin,
cryptoxanthin.

Among the antioxidants capable of neutralizing singlet oxygen, there may also be mentioned nucleosides and their derivatives.

The nucleosides (for example adenosine, guanosine, cytidine, thymidine and uridine and the corresponding deoxyribose derivatives) are especially those derived from the combination of a purine or pyrimidine base chosen from adenine, guanine, cytosine, thymine and uracile (abbreviated A, G, C, T, U) and a pentose (especially ribose and deoxyribose) The nuclooside derivatives are for example mono- di- or triphosphates, and especially 3'- and/or 5'-phosphates, as well an the oligo nucleotides having for example up to 20 nucleotide units.

In the composition of the invention, the proportion by weight of product having a peroxidase activity capable of reducing organic peroxides may vary from 0.005% to 5%, and in particular from 0.01% to 3%.

The proportion by weight of antioxidant capable of neutralizing singlet oxygen may vary for example from 0.005% to 3%, and in particular from 0.01% to 1%.

The relative proportions of peroxidase and anti-singlet oxygen may be determined in each case by simple routine experiments in which the relative proportions giving favourable results (synergy) are selected, for example in the ODC induction test described by R. L. Binder at al., publication mentioned above.

Generally, the peroxidase/anti-singlet oxygen weight ratio may vary for example from 0.001 to 0.3. This ratio is defined here arbitrarily for a product with a peroxidase activity having an activity corresponding to 80 enzymatic units per mg. It in therefore easy to adapt this ratio in the came of a product with peroxidase activity having a different titre in enzymatic units. The peroxidase unit is defined below in the experimental section.

For the production of the pharmaceutical or cosmetic forms, according to known techniques, the solubility characteristics of the ingredients will obviously be taken into account, in association with the type of composition desired.

Products having an organic peroxide-reducing peroxidase activity, as well as nucleosides and their derivatives, are generally soluble in hydrophilic, especially aqueous, phases.

The quinoline derivatives, polyphenols and carotenoids are generally soluble in lipophilic phases.

The compositions of the invention may be provided especially in the form of solutions (lotion type compositions), thickened solutions, gals, ointments, emulsions (creams, milks), vesicular dispersions, powders, dense powders, pastes or solid sticks. They may also be packaged, where appropriate in pressure-packs containing a propelling agent permitting application in the form of foams or sprays.

The cosmetic or pharmaceutical compositions of the invention may contain, in addition to the combination of active ingredients described above, the ingredients or adjuvants customarily used in the production of such compositions, and in particular solvents such as water, organic solvents (for example alcohols, oils), or silicones, thickening agents, surface-active agents, polymars, solid fatty substances (for example waxes, lanolin), moisturizing agents, preserving agents, pH-modifying agents, sequestering agents, colouring agents, perfumes, solid fillers (powders and pigments), ultraviolet radiation-absorbing substances, self-tanning agents (such an dihydroxyacetone), and the like.

The compositions in the form of vesicular dispersions contain for example at least one active ingredient incorporated into micelles or lipid double layers, which may encapsulate an aqueous phase, and which are dispersed in an aqueous solvent.

The vesicular dispersions of lipids, especially of ionic or non-ionic amphiphilic lipids, are prepared according to known processes, for example by swelling the lipids in an aqueous solution in order to form spherules dispersed in the aqueous medium, as described in the publication by Banghan, Standish and Watkins, J. Mol. Biol. 13,238 (1965) or in Patents FR 2,315,991 and 2,416,008 by the Applicant. The description of various preparation procedures can also be found in "Les liposomes en biologic callulaire et pharmacologie", Inserm/John Libbery Eurotext Edition, 1987, pages 6 to 18.

The composition of the invention may contain, in addition to the combination described above, other antioxidants such as ascorbic acid, magnesium ascorbylphosphate, $\alpha$, $\beta$, $\gamma$ and/or $\delta$-tocopherols, bilirubin, biliverdine, $C_1$–$C_{10}$ alkyl esters of glutathione, and the like.

The compositions of the invention are especially cosmetic or pharmaceutical compositions which protect the human epidermis, the hair and the mucous membranes, makeup compositions for the skin and superficial body growths, compositions for buccodental use such as dentifrices, or ophthalmic compositions such as collyria.

When the cosmetic composition according to the invention is used for protecting the hair, it may be provided in the form of shampoos, lotions, gals or compositions to be rinsed, to be applied before or after shampooing, before or after dyeing or bleaching, or before, during or after permanent waving or hair straightening treatment. It may also be provided in the form of hair-styling or treating lotions or gals, lotions or gals for blowdrying or hair setting, hair lacquers, compositions for permanent waving or hair straightening, or compositions for dyeing or bleaching the hair.

When the composition of the invention is used as makeup product for the eyelashes, the eyebrows or the skin, it is provided for example in the form of creams for treating the epidermis, foundations, lipsticks, eyeshadows, blushers, eyeliners or mascaras.

The compositions of the invention, and more particularly the makeup compositions and the anti-sun compositions may contain pigments of metallic oxides such as titanium, zinc, cerium or zirconium oxides, generally at a concentration of between 0.1 and 15%, and in particular between 0.5 and 10% by weight relative to the total weight of the composition. These pigments are preferably used in the form of nanopigments with a mean diameter of loan than 100 nm, generally of between 5 and 50 nm. These nanopigments may be optionally coated. The coated pigments are pigments which have undergone one or more surface treatments of chemical, electronic and/or mechanical nature, with compounds such as amino acids, beeswax, fatty acids, fatty alcohols, anionic surface-active agents, lecithins, fatty acid salts (salts of sodium, potassium, zinc, iron or aluminium), metallic alkoxides (especially of titanium or aluminium), polyethylene, silicones, proteins (for example collagen, elastin), alkanolamines, silicon oxides, metallic oxides or sodiumhexametaphosphate; see on this subject Cosmetics and Toiletries, February 1990, Vol.105, pp.53–64.

When the composition of the invention is a pharmaceutical composition, it may be provided especially in the form of an emulsion (milk or cream), gal, lotion, ointment, vesicular dispersion, and may contain, in addition to the combination described above, another pharmaceutical active ingredient.

By virtue of the synergistic peroxidase+anti-singlet oxygen combination, the compositions of the invention constitute cosmetic or pharmaceutical compositions intended to be applied especially to the skin, superficial body growth, mucous membranes, which make it possible especially to prevent and treat the damage caused by the free radicals induced especially by atmospheric pollutants and by ultraviolet radiation. In particular, the cosmetic compositions of the invention make it possible to prevent or treat especially the phenomenon of accelerated aging of the skin. The compositions of the invention make it possible, in addition, to prevent or limit the risks of skin cancers induced by ultraviolet radiation.

One of the additional advantages of the antioxidant combination according to the invention in that it makes it possible to inhibit or decrease the photoinduced reaction which appears when pigments of metallic oxides are exposed to light, and which in detrimental to the stability of the compositions, in particular when the latter also contain lipids.

The subject of the invention is also the use, in combination, of at least one product with peroxidase activity capable of reducing organic peroxides and of at least one antioxidant capable of neutralizing singlet oxygen, as synergistic active combination in the preparation of a cosmetic or pharmaceutical composition intended to prevent or treat the cellular damage caused by the free radicals induced especially by atmospheric pollutants and/or by ultraviolet radiation, and/or intended to combat the phenomenon of accelerated aging of the skin, or to prevent or limit the risks of photoinduced skin tumours.

The subject of the invention is also a cosmetic treatment process which makes it possible to combat the aesthetic damage caused on the skin and the hair by the free radicals induced especially by atmospheric pollutants and by ultraviolet radiation, characterized by the fact that a composition containing the synergistic combination which has been described above is applied to the skin or the hair.

The following examples illustrate the invention.

In these examples, the origin or nature of the ingredients is the following:

Lactoperoxidase (abbreviated LPO): in the form of a powder; obtained from the company Sederma (France).

Ethoxyquins: mixture of monomer, dimer and polymers of 6-ethoxy-1,2-dihydro-2,2,4-trimethylquinoline marketed under the nano Santoquin by the company Monsanto Guanosines: obtained from Pharma Waldhol Compound A: non-ionic amphiphilic compound of formula:

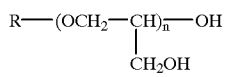

in which R is a hexadecyl radical and n has a mean statistical value equal to 3, Hydroviton: mixture of amino acids, hydrating ingredients for the skin and sodium lactate, allantoin (buffer), marketed by Dragoco, Sipol wax: partially oxyethylenated cetyl stearyl alcohol, marketed by Sinnova-France, Carbopols: cross-linked carboxyvinyl polymers marketed by Goodrich.

EXAMPLE 1

O/W Emulsion

| | |
|---|---|
| Lactoperoxidase (LPO) | 0.05% |
| Ethoxyquine | 0.26% |
| Polyethylene glycol monostearate 50 EO (ICI) | 1.5% |
| Mixture of diglycerol mono- and distearate (Dubois Stearin Industries, France) | 1.5% |
| Vaseline oil | 24% |
| Cetyl alcohol | 2.5% |
| Water q.s | 100% |

This emulsion constitutes a cream. To prepare it, the aqueous phase in poured into the fatty phase at 80° C., with stirring.

This composition is applied to the face.

EXAMPLE 2

Body Care Fluid

A carrier in the form of a dispersion of lipid spherules, of the following composition (in % relative to the final composition), is first prepared in a known manner:

| | |
|---|---|
| Compound A | 4.5% |
| Cholesterol | 4.5% |
| Dicetyl phosphate | 1.0% |
| Methyl para-hydroxybenzoate | 0.3% |
| Sterile demineralized water | 30% |

For that, the first three ingredients are mixed by melting at 100° C., under a nitrogen atmosphere, cooled to 80° C. and then homogenized by means of a Virtis type ultradispersing device. The water and the preserving agent are then added. The dispersion in adjusted to room temperature and 0.1% of lactoperoxidase is added thereto, followed by the phase A below:

| Phase A | |
|---|---|
| Perfume | 0.4% |
| Sunflower oil | 10% |
| Paraffin oil | 4% |
| Vitamin F | 2% |
| Soyabean lecithin | 1% |
| Ascorbyl palmitate | 1% |
| Hexadecylamine salicylate | 0.2% |
| Ethoxyquine | 0.8% |

The mixture is homogenized by means of an ultradispersing device, the phase B, consisting of:

| | |
|---|---|
| "Carbopol 940" | 0.4% |
| Demineralised water | 79.7% | in then dispersed.

The whole is finally neutralized by means of 0.4% triethanolamine.

EXAMPLE 3

Beauty Milk for the Body

An oil-in-water (O/W) emulsion of the following composition was prepared:

| | |
|---|---|
| Purcellin oil (Dragoco) | 2 g |
| Vaseline oil | 6 g |
| Oleyl alcohol | 1 g |
| Isopropyl myristate | 1.5 g |
| Glycerin monostearate | 2 g |
| Stearin | 1.4 g |
| Cetyl alcohol | 0.1 g |
| Perfume | 0.9 g |
| Carbopol 941 | 0.35 g |
| Pure triethanolamine | 1.05 g |
| Butyl para-hydroxybenzoate | 0.04 g |
| Preserving agent | 0.3 g |
| Propylene glycol | 5 g |
| Hydroviton | 1.5 g |
| Guanosine | 0.5 g |
| Colorant F.D.C. blue 1 (Kohnstamn) at 1% in water | 0.03 g |
| Lactoperoxidase | 0.1 g |
| Demineralized water | 71.55 g |

EXAMPLE 4

Body Cream

An O/W emulsion of the following composition is prepared:

| | |
|---|---|
| Cetyl alcohol | 0.5 g |
| Sipol wax | 5 g |
| Glycerol monostearate | 1.5 g |
| Vaseline oil | 6 g |
| Isopropyl myristate | 3 g |
| Glycerin | 10 g |
| Perfume | 0.2 g |

-continued

| | |
|---|---|
| Guanosine | 1.5 g |
| Lactoperoxidase | 0.2 g |
| Water q.s. | 100 g |

EXAMPLE 5

Body Cream

An O/W emulsion of the following composition is prepared:

| | |
|---|---|
| Sipol wax | 6 g |
| Glycerol monostearate | 1.5 g |
| Sodium stearate | 0.8 g |
| Vaseline oil | 6 g |
| Isopropyl palmitate | 2 g |
| Ethoxyquine | 1 g |
| Glycerin | 15 g |
| Perfume | 0.3 g |
| Lactoperoxidase | 2 g |
| Water q.s. | 100 g |

EXAMPLE 6

Dermopharmaceutical Cream

| | |
|---|---|
| Phase A | |
| Polyethylene glycol stearate sold under the name "Myrj 49" by the company ICI | 1.75 g |
| Glycerol stearate and polyethylene glycol stearate sold under the name "Arlacel 165" by the company ICI | 1.75 g |
| Cetyl alcohol | 0.6 g |
| Stearyl alcohol | 0.6 g |
| Vaseline oil | 17 g |
| Stearic acid | 2.5 g |
| Phase B | |
| Cross-linked polyacrylic acid sold under the name "Carbopol 941" by the company Goodrich | 0.4 g |
| Lactoperoxidase | 0.1 g |
| Glycerin | 3 g |
| Methyl para-hydroxybenzoate | 0.1 g |
| Tetrasodium salt of ethylendiaminetetraacetic acid | 0.1 g |
| Triethanolamine (20% aqueous solution) | 0.5 g |
| Water | 66.53 g |
| Phase C | |
| Ethoxyquine | 0.05 g |
| Retinoic acid | 0.02 g |
| Isopropyl myristate | 5 g |

The constituents of the fatty phase A are mixed at 70° C.

The constituents of the aqueous phase B, heated to 70° C., are solubilized with stirring.

The aqueous phase B is added to the fatty phase A with stirring. Ethoxyquine and retinoic acid, solubilized in isopropyl myristate (Phase C) are added to the emulsion obtained.

An anti-aging treatment cream is obtained which can be applied to the face.

EXAMPLE 7

Anti-wrinkle Dermapharmaceutical Gel

The following compounds are mixed at room temperature and with stirring:

| | |
|---|---|
| Synperonic PE/L62* | 0.2 g |
| Propylene glycol | 4 g |
| Ethoxyquine | 0.1 g |
| Lactic acid | 1 g |
| Tetrasodium salt of ethylenediaminetetraacetic acid | 0.1 g |
| Lactoperoxidase | 0.4 g |
| Phenoxyethanol | 0.25 g |
| Water q.s. | 100 g |

*Marketed by the company ICI: block polymer polyoxyethylene/polyoxypropylene/polyoxyethylene: Poloxamer 182 (CFTA).

1 g of cross-linked polyacrylic acid sold under the name Carbopol 940 by the company Goodrich in added to the dispersion, and then sodium hydroxide is added in order to adjust the pH to 5.

The gel obtained in applied to the face and the neck.

EXAMPLE 8

Protective Care Cream

| | |
|---|---|
| "Sinnowax AO" | 5 g |
| Glycerol stearate | 1 g |
| Cetyl alcohol | 1 g |
| Jojoba oil | 6 g |
| Linoleic acid | 6 g |
| "MT 100 T" (TiO$_2$) | 5 g |
| Ethoxyquine | 1 g |
| Lactoperoxidase | 0.04 g |
| Preservatives | q.s. |
| Water q.s. | 100 g |

The fatty phase is heated to 80° C. Titanium oxide in added.

The aqueous phase is poured, with stirring at 80° C., into the fatty phase.

This composition, in the form of a cream, in applied to the face.

Sinnowax AO, marketed by the company Henkel, is a mixture of cetyl stearyl alcohol and oxyethylenated cetyl stearyl alcohol containing 33 mols of ethylene oxide.

MT 100 T in the trade name for a titanium oxide marketed by the company Tayca.

PHARMACOLOGICAL STUDY

The text used consists in evaluating the induction of the formation of ODC by irradiation according to a technique analogous to that described by R. L. Binder et al., publication mentioned above.

The products to be evaluated are studied in the form of a cream containing 30 u/g of lactoperoxidase and 1% othoxyquine.

It is recalled that one unit of lactoperoxidase forms 1 mg of purpurogallin from pyrogallol in 20 seconds (20° C.) at pH 6.0. The formula at 30 u/g contains 0.039% by weight of lactoperoxidase.

This cream was compared with a cream containing only ethoxyquine or containing only lactoperoxidase, at the same concentration.

RESULTS

Ethoxyquine alone is without significant effect on the formation of ODC, compared with a placebo. Lactoperoxidase alone results in a substantial increase (72% in the present case) in the formation of ODC, relative to a placebo.

In contrast, the combination of these two ingredients results in a substantial decrease (−54% in the present case) in the formation of ODC relative to the placebo.

What is claimed is:

1. A method of reducing damage caused to healthy skin or mucous membranes by free radicals, comprising applying to the healthy skin or mucous membrane a composition comprising at least one product having a peroxidase activity capable of reducing organic peroxides and at least one antioxidant capable of neutralizing singlet oxygen, wherein said composition is free of peroxide, wherein said product having a peroxidase activity is present in an amount of from 0.005 to 5.0% by weight, said antioxidant is present in an amount of from 0.005 to 3.0% by weight and a weight ratio of said product having a peroxidase activity to said antioxidant is from 0.001 to 0.3, wherein said at least one product having a peroxidase activity capable of reducing organic peroxides is lactoperoxidase, and wherein said antioxidant is selected from the group consisting of quinolines, polyphenols, and carotenoids.

2. A process for reducing aesthetic damage caused to healthy skin or hair by free radicals, comprising applying to the healthy skin or hair a composition comprising at least one product having a peroxidase activity capable of reducing organic peroxides and at least one antioxidant capable of neutralizing singlet oxygen, wherein said composition is free of peroxides, wherein said product having a peroxidase activity is present in an amount of from 0.005 to 5.0% by weight, said antioxidant is present in an amount of from 0.005 to 3.0% by weight and a weight ratio of said product having a peroxidase activity to said antioxidant is from 0.001 to 0.3, wherein said at least one product having a peroxidase activity capable of reducing organic peroxides is lactoperoxidase, and wherein said antioxidant is selected from the group consisting of quinolines, polyphenols, and carotenoids.

3. A method according to claim 1, wherein said antioxidant is quinoline.

4. A method according to claim 1, wherein said antioxidant is selected from the group consisting of ethoxyquine or an ethoxyquine compound of the following formula (I):

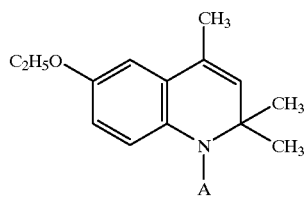

(I)

wherein A represents a group —CO—B, in which B represents a group selected from the group consisting of:

(1) a group $(CHOR')_nR$ in which R' represents a hydrogen atom, an acyl, alkyl or aralkyl group, R is a hydroxymethyl, carboxyl, carboxyalkyl, carboxyaryl, carboxyarylalkyl, carboxamide or —COR''' group, R''' representing an ethoxyquine residue of formula (I) less the substituent A or R''' representing —CH$_2$OR'', R'' being an acyl, aralkyl or alkyl radical and n being an integer from 2 to 6;

(2) a group —(CHR'''')$_m$N$^+$R$_1$R$_2$R$_3$X$^-$ in which R'''' represents a hydrogen atom, an optionally substituted heterocyclic, aralkyl, aryl or alkyl radical, or R'''' represents —(CH$_2$)$_q$COOH where q is a number which may vary from 1 to 3, R$_1$, R$_2$ and R$_3$ independently representing a hydrogen atom, an aryl radical, a heterocyclic aryl radical, a substituted or unsubstituted cycloalkyl or alkyl radical, X$^-$ being an anion and m being an integer from 1 to 6;

(3) a group —(CHR'''')$_m$NR$_1$R$_2$, where R'''', R$_1$, R$_2$ and m have the meanings stated above;

(4) a group NR'$_1$R'$_2$ in which R'$_1$ and R'$_2$ independently represent a substituted or unsubstituted aryl, heterocyclic aryl, cycloalkyl or alkyl group or alternatively R'$_1$ and R'$_2$ represent —H or form a heterocyclic group with the nitrogen atom to which they are attached;

(5) a group —OR$_4$ in which R$_4$ represents an aryl, alky, polyhydroxyalkyl or cycloalkyl group or a group of formula

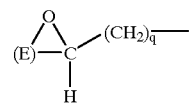

where E represents a group:

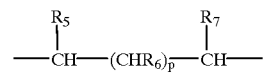

in which R$_5$, R$_6$ and R$_7$ independently represent a hydrogen atom or a radical —CH$_2$OH, —CH$_2$O acyl, —OH, —O acyl, —NH acyl, —NH$_2$, N$^+$H$_3$X$^-$, X$^-$ being defined as above, or alternatively R$_5$, R$_6$ and R$_7$ represent a group —COOR$_8$, R$_8$ representing a hydrogen atom, a substituted or unsubstituted aralkyl, aryl, cycloalkyl or alkyl group, p is a number equal to 1 or 2 and q is equal to 0 or 1; and (6) a halogen atom, or alternatively A represents a group:

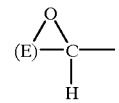

in which E is defined as above.

5. A method according to claim 1, wherein said antioxidant is a polyphenol comprising at least one diphenolic aromatic ring, wherein phenol groups of said polyphenol may be optionally etherified or esterified.

6. A method according to claim 5, wherein said polyphenol is a flavonoid.

7. A method according to claim 6, wherein said flavonoid is a compound of the general formula (II):

(II)

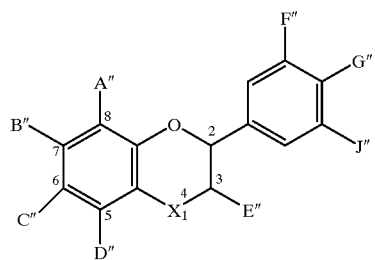

or (III):

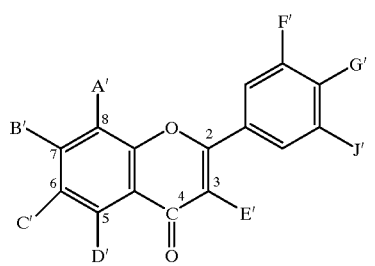

in which A", B", C" and D", independently of each other, represent H or OH; E" represents H, OH or OX', where X' represents:

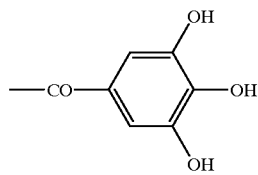

F", G", J" represent, independently of each other, H or OH; and $X_1$ represents —$CH_2$—, —CO— or —CHOH—, wherein at least two of the groups A", B", C" and D" or at least two of the radicals F", G" and J" designate a hydroxyl group, A', C' and D', independently of each other, represent H, OH or $OCH_3$;

E' represents H, OR', R' represents the residue of a sugar of formula R'OH;

B', F', G' and J', independently of each other, represent H, OH, $OCH_3$ or —$OCH_2$—$CH_2$—OH, wherein at least two of the groups A', B', C' and D' do not designate —H or wherein at least one of the groups F', G' and J' does not designate —H.

8. A method according to claim 6, wherein said flavonoid is selected from the group consisting of taxifoline, catechin, epicatechin, eriodictyol, naringenin, rutin, troxerutin, chrysin, tangeretine, luteolin, epigallocatechin, epigallocatechin gallate, quercetin, fisetin, kaempferol, galangin, gallocatechin and epicatechin gallate.

9. A method according to claim 5, wherein said polyphenol is a (2,5-dihydroxyphenol) alkylcarboxylic acid of formula (IV) or an ester or amide thereof:

(IV)

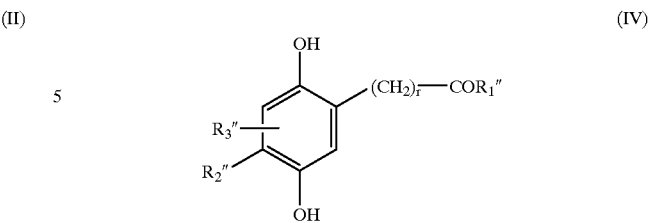

in which:

$R''_1$ represents —O—Alc, OH or —N(r')(r"), Alc being a linear or branched $C_1$–$C_{20}$ alkyl optionally substituted by one or more hydroxyl or alkoxy groups, or Alc being a $C_2$–$C_{20}$ alkenyl, r' and r" independently represent H, $C_1$–$C_{20}$ alkyl, $C_2$–$C_6$ hydroxyalkyl or $C_3$–$C_6$ polyhydroxyalkyl, or alternatively r' and r" together form, with the nitrogen atom to which they are attached, a heterocycle, r is a number, including zero, such that the chain —$(CH_2)_r$—$COR_1$ comprises at most 21 carbon atoms, $R''_2$ and $R''_3$ independently represent H or a $C_1$–$C_4$ alkyl, it being possible for $R''_2$ to represent, in addition, a $C_1$–$C_4$ alkoxy.

10. A method according to claim 5, wherein said polyphenol is an ester or a amide of caffeic acid, wherein said ester is represented by the following formula (V):

(V)

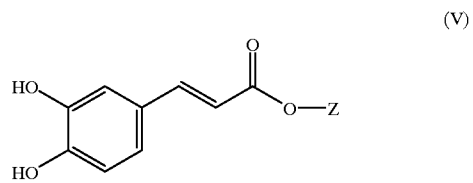

in which Z represents a $C_1$–$C_8$ alkyl or the residue of a phytol and said amide is represented by the following formula (VI):

(VI)

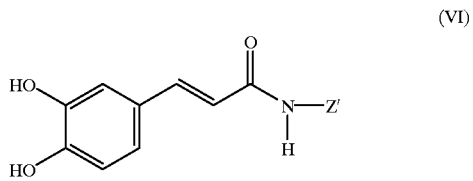

in which Z' represents a $C_1$–$C_8$ alkyl.

11. A method according to claim 1, wherein said antioxidant is a carotenoid selected from the group consisting of all-trans-betacarotene, alpha-carotene, gamma-carotene, delta-carotene, decapreno-beta-carotene, dodecapreno-beta-carotene, lycopene, zeaxanthin, astaxanthin, violaxanthin, lutein, bixin, canthaxanthin, and cryptoxanthin.

* * * * *